United States Patent [19]
Yamamoto et al.

[11] Patent Number: 6,033,693
[45] Date of Patent: Mar. 7, 2000

[54] CALCIUM PRODUCT AND A RAW MATERIAL FOR THE PRODUCT AND PROCESSES FOR THEIR PREPARATION

[75] Inventors: Kozo Yamamoto, Ibaraki; Masayoshi Yanoshi, Osaka, both of Japan

[73] Assignee: Osaka Fujijin Co., Ltd., Osaka-fu, Japan

[21] Appl. No.: 09/179,452

[22] Filed: Oct. 27, 1998

[30] Foreign Application Priority Data

Oct. 27, 1997 [JP] Japan ................................ 9-294252

[51] Int. Cl.$^7$ ............................................ A23L 1/304
[52] U.S. Cl. ..................... 426/72; 426/455; 426/456; 426/459; 426/466; 426/520; 426/626; 426/648
[58] Field of Search .................. 426/74, 455, 456, 426/459, 466, 520, 626, 648

[56] References Cited

U.S. PATENT DOCUMENTS 5,296,246  3/1994  Inoue et al. .
5,700,503  12/1997  Hirota ........................... 426/456

FOREIGN PATENT DOCUMENTS 60037953  2/1985  Japan .
62101699  5/1987  Japan .
2-200164  8/1990  Japan .

OTHER PUBLICATIONS

Poneros–Schneier et al, "Bioavailability of Calcium from Sesame Seeds, Almond Powder, Whole Wheat Bread, Spinach and Nonfat Dry Milk in Rats", Jounal of Food Science—Vol. 54, No. 1, pp. 150–153, 1989.

Ishi, et al., "Extraction of calcium, oxalate and calcium oxalate crystals from sesame seeds", abstract of Bunseki Kagaku, vol. 43, No. 2, pp. 6–46, 1994.

*Primary Examiner*—Helen Pratt
*Attorney, Agent, or Firm*—Nikaido Marmelstein Murray & Oram, Ltd

[57] ABSTRACT

This invention provides a calcium product which can be absorbed into the living body at a high ratio and which is prepared by extracting calcium from ashes using an acidic aqueous solution, the ashes containing small amounts of oxalic acid and phytic acid and being obtained by calcination of sesame testae.

15 Claims, 1 Drawing Sheet

CALCIUM PRODUCT AND A RAW MATERIAL FOR THE PRODUCT AND PROCESSES FOR THEIR PREPARATION

TECHNICAL FIELD

The present invention relates to a calcium product (sesame mineral), a process for preparing the calcium product, a raw material for preparing the calcium product, a process for preparing the raw material, and a method for extracting calcium from the testae of sesame. The calcium product (sesame mineral) of the present invention is useful, for example, as a food, more specifically as a mineral food.

BACKGROUND ART

The sesame contains about 2% of oxalic acid (including an oxalic acid base such as one existing as a metal salt) most of which is present in its testa. The calcium of sesame exists as calcium oxalate in its testa. The oxalic acid contained in foods binds to calcium, adversely affecting the ratio of absorption in the living body (hereinafter referred to as "internal absorption ratio"). A number of researches were reported on the internal absorption ratio of calcium oxalate in spinach. The internal absorption ratio of calcium in spinach is reportedly in the range of approximately from 1/5 to 1/10 the internal absorption ratio of calcium in cabbage with a low content of oxalic acid.

The sesame is a food with a high content of phytic acid (including a phytic acid base such as one existing as a metal salt). Generally phytic acid is predominantly contained in grains, beans, seeds or the like. Reportedly phytic acid relatively firmly binds to mineral components such as calcium, magnesium, iron, zinc or the like, impairing the internal absorption ratio of minerals in grains, beans, seeds or the like. According to numerous reports, when a large amount of phytic acid is ingested, the mineral simultaneously taken in is almost excreted as adsorbed on the phytic acid and scarcely left.

Despite the great popularity of calcium in recent years, attention has not been drawn to the calcium contained in the testae of sesame presumably for the above-mentioned reason. In such situation, the present inventors made attempts to recover free calcium (calcium not bonded to oxalic acid or phytic acid) from the testae of sesame and found it difficult to simultaneously conduct a first step of decomposing calcium oxalate to give free calcium and a second step of removing the phytic acid bonded to mineral.

SUMMARY OF THE INVENTION

An object of the present invention is to provide a calcium product (sesame mineral) which can be absorbed into the living body at a high ratio.

Another object of the invention is to provide a process for preparing a calcium product (sesame mineral) from the testae of sesame and a raw material for the calcium product.

A further object of the invention is to provide a method of recovering calcium with ease from the testae of sesame.

The inventors conducted extensive research and found the following.

(1) When the calcium component recovered directly from the testae of sesame is ingested as a calcium product, it is absorbed into the living body at a low ratio.

(2) The internal absorption ratio is hindered by the oxalic acid and phytic acid derived from the testae of sesame.

(3) When the testae of sesame are calcined, the oxalic acid and phytic acid are removed.

(4) When extracted using an acidic aqueous solution, a calcium component can be easily recovered from the ash obtained by calcination of sesame testae.

(5) The calcium component thus recovered is easily absorbed into the living body.

Based on these findings, the present invention was completed.

According to the invention, there are provided a raw material for preparing a calcium product (sesame mineral), the raw material being prepared by calcining sesame testae (e.g. at a temperature of not lower than 300° C., preferably not lower than 900° C. for 30 minutes or longer), and more particularly a raw material for preparing the calcium product (sesame mineral), the raw material containing oxalic acid in an amount of not greater than 1700 mg/100 g (preferably being free of oxalic acid) and/or phytic acid in an amount of not greater than 170 mg/100 g (preferably being free of phytic acid).

According to the invention, there is also provided a calcium product (sesame mineral) containing the calcium component recovered from said raw material (especially a calcium product containing calcium in an amount of at least 5 g/100 g).

According to the invention, there is also provided a process for preparing a calcium product (sesame mineral), the process comprising the steps of extracting a calcium component from said raw material using an acidic aqueous solution and recovering the calcium component.

According to the invention, there is also provided a method of extracting calcium from sesame testae, the method comprising the step of extracting calcium from said raw material using an acidic aqueous solution as an extraction solution.

Figure 1:
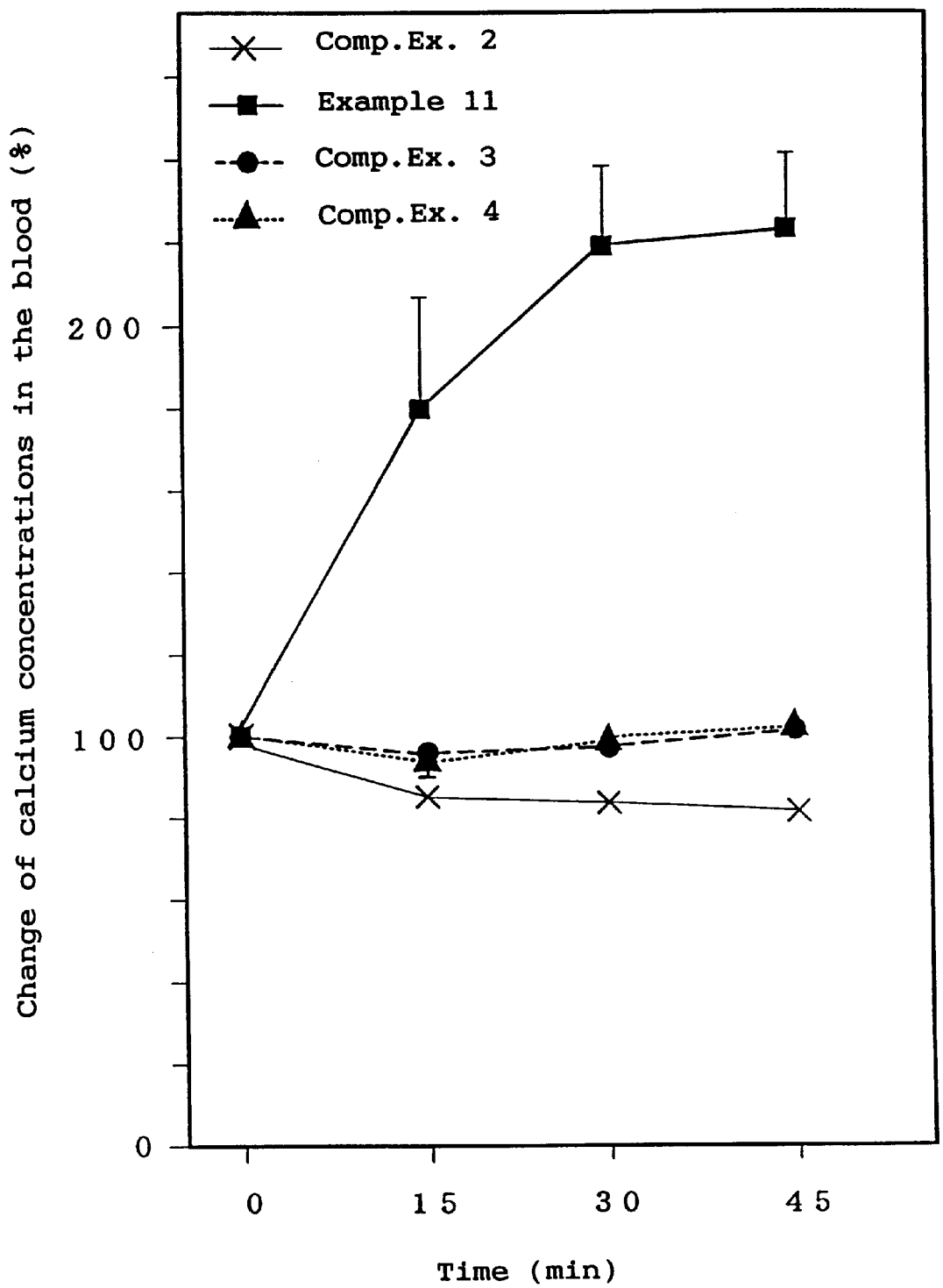
FIG. 1 is a graph showing the change of calcium concentrations in the blood of rats to which the calcium products (sesame minerals) of Example 11 and Comparative Examples 2–4 have been intraintestinally administered.

DETAILED DESCRIPTION OF THE INVENTION (Sesame testa)

The sesame is a seed of an annual plant pertaining to Pedaliaceae. Sesame has been used for expression of oil and has been processed into food materials such as ground sesame, parched sesame, etc. In the practice of the invention, the testae of sesame employed for these applications can be used.

The sesame is classified into black sesame, white sesame, yellow sesame, golden sesame and the like. The testae of all types of sesame can be used in the invention.

The sesame testae can be recovered by peeling using, e.g. a rotary shifter, a rotary screen, a gravity separator (air classifier) or the like.

The sesame testae usually contain oxalic acid in an amount of at least 1800 mg/100 g and phytic acid in an amount of at least 180 mg/100 g. When the calcium component recovered directly from sesame testae (e.g. by extraction using an acidic aqueous solution) is used as a calcium product (e.g. a mineral food), the internal absorption of calcium is inhibited by the oxalic acid and phytic acid derived from the sesame testae.

[Raw material for a calcium product]

Calcination of sesame testae gives ash containing small amounts of oxalic acid and/or phytic acid and a large amount of calcium. The ash with low contents of oxalic acid and/or phytic acid and a high content of calcium is useful as a raw material for a calcium product (sesame mineral).

In a preferred mode for carrying out the invention, ashes to be used as a raw material for a calcium product include those which are prepared by calcining sesame testae and which contain calcium in an amount of at least 25 g/100 g, preferably at least 30 g/100 g, usually not greater than 40 g/100 g.

In a preferred mode for carrying out the invention, ashes to be used as a raw material for a calcium product include those which are prepared by calcining sesame testae and which contain oxalic acid in an amount of not greater than 1700 mg/100 g, preferably not greater than 1200 mg/100 g, more preferably not greater than 700 mg/100 g, especially preferably not greater than 400 mg/100 g, most preferably substantially zero.

In a preferred mode for carrying out the invention, ashes to be used as a raw material for a calcium product include those which are prepared by calcining sesame testae and which contain phytic acid in an amount of not greater than 170 mg/100 g, preferably not greater than 120 mg/100 g, more preferably not greater than 70 mg/100 g, especially preferably not greater than 40 mg/100 g, most preferably substantially zero.

The ashes with low contents of oxalic acid and/or phytic acid can be obtained by adjusting the conditions for calcining sesame testae. More specifically, the contents of oxalic acid and/or phytic acid can be reduced by calcination at an elevated temperature or for a prolonged time.

For example, ashes suitable as a raw material for a calcium product are obtainable by calcination of sesame testae at a temperature of 300° C. or higher for 30 minutes or longer (e.g., 60 minutes or longer), preferably 600° C. or higher for 30 minutes or longer (e.g., 60 minutes or longer), more preferably 800° C. or higher for 30 minutes or longer (e.g., 60 minutes or longer), especially preferably 900° C. or higher for 30 minutes or longer, usually 1200° C. or lower for 120 minutes or shorter.

There is no limitation on the atmosphere in calcining sesame testae. For example, ashes suitable as a raw material for a calcium product are obtainable by calcination of sesame testae in the air.

Sesame testae can be calcined, for example, by being indirectly heated or directly heated (e.g. burnt). The calcining apparatus employable in the invention are not limited. For example, a calcining furnace is usable.

[Method of extracting calcium]

An acidic aqueous solution is contacted with a raw material for a calcium product, whereby the calcium component in the raw material can be dissolved out in the aqueous phase. Useful acidic aqueous solutions include, for example, aqueous solutions of at least one of acids such as inorganic acids, e.g. hydrochloric acid, sulfuric acid or the like, or organic acids, e.g. lactic acid, fermented lactic acid, acetic acid or the like. Useful acidic aqueous solutions are not limited and include those having a pH of not higher than 6, preferably not higher than 4.

The aqueous phase having the calcium component dissolved out therein can be separated from the solid phase by decantation, filtration, centrifuging or the like. The aqueous phase is, for example, evaporated to dryness, whereby the calcium component dissolved out in the aqueous phase can be recovered as solids (powder).

[Calcium product (sesame mineral)]

The calcium component recovered from the raw material for a calcium product has low contents of oxalic acid and phytic acid and is useful as a calcium product (sesame mineral).

There is no limitation on the form of the calcium product according to the invention. The calcium product is prepared in the form of, e.g. powders, granules or pellets optionally using an excipient. Optionally the calcium product is prepared as a solution or a dispersion with the product dissolved or dispersed in an arbitrary solvent for foods or in a pharmaceutically acceptable arbitrary solvent.

The calcium component recovered from the raw material for a calcium product has a calcium content of at least about 5 g/100 g, preferably at least about 10 g/100 g, usually not greater than about 20 g/100 g; a potassium content of not greater than about 20 g/100 g, preferably about 3–15 g/100 g; a magnesium content of not greater than about 15 g/100 g, preferably about 1–10 g/100 g; a phosphorus content of not greater than about 10 g/100 g, usually about 0.5–5 g/100 g; each of sodium content, sulfur content, iron content and chlorine content being not greater than about 5 g/100 g, preferably about 0.1–1 g/100 g; each of manganese content and zinc content being not greater than about 20 mg/100 g, preferably about 1–15 mg/100 g; and a copper content being not greater than about 1 mg/100 g, preferably about 0.05–0.5 mg/100 g.

[Effect of the invention]

According to the invention, a calcium product (sesame mineral) can be produced from sesame testae, the calcium product having low contents of oxalic acid and/or phytic acid and being absorbable into the living body at a high ratio. Calcium can be efficiently ingested by the intake of the calcium product (sesame mineral) of the invention.

Examples 1 to 10

[Production of raw material for calcium product (sesame mineral)]

Sesame testae were calcined in the air under the conditions (temperature and time) shown in Table 1 using a calcining furnace, giving ashes. The sesame testae used were those of Chinese growth and were fresh and useful for processing into ground sesame, parched sesame or the like. The amounts of oxalic acid and phytic acid remaining in the obtained ashes were measured by the Vanado-molybdic acid absorptionspectrophotometry. The results are shown in Table 1. As to the raw materials for calcium product in Comparative Example 1, the amounts of oxalic acid and phytic acid in the sesame testae were measured prior to calcination.

The results of Table 1 shows that as the temperature was elevated or the time was prolonged for calcination of sesame testae, the contents of oxalic acid and phytic acid in the obtained ashes were decreased. It was found that ashes free of oxalic acid and phytic acid can be obtained by calcining sesame testae at 900 to 1000° C. for 30 to 60 minutes.

[Production of a calcium product (sesame mineral)]

After the obtained ashes (raw materials for calcium products) were cooled to room temperature, an acidic aqueous solution was gradually added to the ashes with thorough stirring. The aqueous solution used was a 5 to 20% aqueous solution of hydrochloric acid, sulfuric acid, lactic acid, spontaneously fermented lactic acid or acetic acid.

The acid reacted with the ashes to generate a gas (carbon dioxide gas) while the mineral components in the ashes were dissolved out into the solution. The acidic aqueous solution was continuously added until the cease of gas generation.

After the termination of the reaction, the reaction product was left to stand and was separated into an aqueous phase (supernatant) and a solid phase (precipitate). The aqueous phase was collected by decantation and evaporated to dryness to give a calcium product.

TABLE 1

| | Calcining temperature (° C.) | Calcining time (minute) | Residue amount (mg/100 g) | |
|---|---|---|---|---|
| | | | Oxalic acid | Phytic acid |
| Comp. Ex. 1 | — | — | 1800 | 186 |
| Example 1 | 300 | 30 | 1500 | 150 |
| Example 2 | 300 | 60 | 1400 | 130 |
| Example 3 | 500 | 30 | 800 | 80 |
| Example 4 | 500 | 60 | 600 | 63 |
| Example 5 | 700 | 30 | 200 | 23 |
| Example 6 | 700 | 60 | 100 | 5 |
| Example 7 | 900 | 30 | 0 | 0 |
| Example 8 | 900 | 60 | 0 | 0 |
| Example 9 | 1000 | 30 | 0 | 0 |
| Example 10 | 1000 | 60 | 0 | 0 |

TABLE 2

| Component | Content (mg/100 g) | Analytic method |
|---|---|---|
| Calcium | $12.7 \times 10^3$ | Potassium permanganate volumetric method |
| Potassium | $9.60 \times 10^3$ | Atomic absorption spectrophotometry |
| Magnesium | $4.44 \times 10^3$ | Atomic absorption spectrophotometry |
| Phosphorus | $3.14 \times 10^3$ | Vando-molybdic acid absorption spectrophotometry |
| Sodium | $0.641 \times 10^3$ | Atomic absorption spectrophotometry |
| Sulfur | $0.33 \times 10^3$ | Barium sulfate weighing inethod |
| Iron | $0.309 \times 10^3$ | o-Phenanthroline absorption spectrophotometry |
| Chlorine | $0.229 \times 10^3$ | Mohr's method |
| Manganese | 7.98 | Atomic absorption spectrophotometry |
| Zinc | 7.61 | Atomic absorption spectrophotometry |
| Copper | 0.10 | Atomic absorption spectrophotometry |

Example 11

[Production of a calcium product (sesame mineral)]

The sesame testae (5 kg) of the type used in examples 1 to 10 were calcined at 900° C. for 1 hour using a calcining furnace, giving 1 kg of ashes. The ashes were placed into a reaction vessel. Thereafter, 2.5 liter of a 15% aqueous solution of acetic acid was gradually added to the reaction vessel with stirring to completely dissolve out mineral components into the aqueous phase. The solution was filtered to recover the filtrate. The filtrate was evaporated by heating to dryness to give 530 g of solids containing mineral components.

The mineral components in the solids thus obtained were analyzed to determine the composition. The analysis results and the analytic method are shown in Table 2.

[Change of calcium concentration in the rats' blood after intraintestinally administering a calcium product]

The obtained calcium product was intraintestinally administered to rats in the form of an aqueous solution or an aqueous suspension containing 2 wt % of calcium. Then, the varied calcium concentrations in the blood of rats were measured.

The blood was collected from the jugular vein of anesthetized Wistar-strain rats (weighing 214 to 232 g) with the gastropyloric portion and the ileum bottom ligated together. Into an intestine loop was injected 25 ml/kg (500 mg/kg as Ca) of an aqueous solution or suspension (2% Ca content) of the calcium product with a pH adjusted to 7.2. Fifteen minutes, 30 minutes and 45 minutes after injection, the blood was collected from the rats' jugular vein. The blood plasma was separated from the collected blood and then the calcium concentration of the blood was measured with an autoanalyzer (7070 type: product of Hitachi Ltd.). Three rats were used in each group.

FIG. 1 shows the results of measurement as an average value±S.D., namely the percent calcium concentration in the blood based on the calcium concentration (100%) in the blood prior to administration. FIG. 1 also shows the results of measurement after administration of calcium products such as the calcium component recovered directly from non-calcined sesame testae (Comparative Example 2), calcium carbonate as a pharmaceutical preparation (Comparative Example 3) and the calcium component recovered from the shell of sea urchin (Comparative Example 4).

The calcium products in the Examples illustrative of the present invention show the ratios of absorption into the blood approximately twice the ratios thereof regarding Comparative Examples.

We claim:

1. A composition comprising calcined sesame testae, wherein the composition contains no more than 1700 mg of oxalic acid per 100 g of composition.

2. The composition according to claim 1, wherein the composition is substantially free of oxalic acid.

3. The composition according to claim 1, wherein the composition contains no more than 170 mg of phytic acid per 100 g of composition.

4. The composition according to claim 3, wherein the composition is substantially free of phytic acid.

5. A process for preparing a calcium-containing product, the process comprising extracting a calcium component from the composition of claim 1 using an acidic aqueous solution, and recovering the calcium component.

6. The process according to claim 5, wherein the acidic aqueous solution is at least one solution selected the group consisting of hydrochloric acid, sulfuric acid, lactic acid, fermented lactic acid and acetic acid.

7. The process according to claim 5, wherein the acidic aqueous solution has a pH of not higher than 6.

8. A process, comprising extracting a calcium component from the composition of claim 1 using an acidic aqueous solution as an extraction solution.

9. The composition according to claim 1, wherein the sesame testae are calcined at 300° C. or higher for 30 minutes or longer.

10. A. process for preparing a composition comprising calcined sesame testae, the process comprising the step of calcining sesame testae wherein the sesame testae are calcined at 300° C. or higher for 30 minutes or longer.

11. The process according to claim 10, wherein the sesame testae are calcined at 900° C. or higher for 30 minutes or longer.

12. A calcium-containing product which is prepared from the composition according to claim 1, wherein the calcium-containing product contains calcium in an amount of at least 5 g/100 g.

13. A calcium-containing product according to claim 12, which has a calcium content of 5–20 g/100 g.

14. The calcium-containing product according to claim 13, wherein the product additionally has a potassium content of not greater than 20 g/100 g, a magnesium content of not greater than 15 g/100 g, a phosphorus content of not greater than 10 g/100 g, each of a sodium content, a sulfur content, an iron content and a chlorine content of not greater than 5 g/100 g, each of a manganese content and a zinc content of not greater than 20 mg/100 g and a copper content of not greater than 1 mg/100 g.

15. The calcium-containing product according to claim 13, wherein the product additionally has a potassium content of 3–15 g/100 g, a magnesium content of 1–10 g/100 g a phosphorus content of 0.5–5 g/100 g, each of a sodium content, a sulfur content, an iron content and a chlorine content of 0.1–1 g/100 g, each of a manganese content and a zinc content of 1–15 mg/100 g and a copper content of 0.05–0.5 mg/100 g.

* * * * *